United States Patent
Capote

(10) Patent No.: US 9,730,806 B2
(45) Date of Patent: Aug. 15, 2017

(54) SPINAL IMPLANT SYSTEM AND METHOD

(71) Applicant: Warsaw Orthopedic, Inc., Warsaw, IN (US)

(72) Inventor: Cristian A. Capote, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 159 days.

(21) Appl. No.: 14/524,989

(22) Filed: Oct. 27, 2014

(65) Prior Publication Data

US 2016/0113776 A1    Apr. 28, 2016

(51) Int. Cl.
  *A61F 2/44*    (2006.01)
  *A61F 2/46*    (2006.01)
  *A61F 2/30*    (2006.01)

(52) U.S. Cl.
  CPC ............ *A61F 2/447* (2013.01); *A61F 2/4611* (2013.01); *A61F 2002/30507* (2013.01); *A61F 2002/30523* (2013.01); *A61F 2002/30538* (2013.01); *A61F 2002/4627* (2013.01); *A61F 2002/4629* (2013.01)

(58) Field of Classification Search
  CPC .. A61F 2002/30579; A61F 2002/30523; A61F 2002/30525; A61F 2002/30527; A61F 2002/30601
  See application file for complete search history.

(56) References Cited

U.S. PATENT DOCUMENTS

| | | |
|---|---|---|
| 7,828,849 B2 | 11/2010 | Lim |
| 7,850,733 B2 | 12/2010 | Baynham et al. |
| 7,875,078 B2 | 1/2011 | Wysocki et al. |
| 7,909,869 B2 | 3/2011 | Gordon et al. |
| 8,062,375 B2 | 11/2011 | Glerum et al. |
| 8,105,358 B2 | 1/2012 | Phan |
| 8,105,382 B2 | 1/2012 | Olmos et al. |
| 8,123,810 B2 | 2/2012 | Gordon et al. |
| 8,133,232 B2 | 3/2012 | Levy et al. |
| 8,147,554 B2 | 4/2012 | Hansell et al. |
| 8,187,332 B2 | 5/2012 | Mcluen |
| 8,382,842 B2 | 2/2013 | Greenhalgh et al. |
| 8,394,145 B2 | 3/2013 | Weiman |
| 8,398,713 B2 | 3/2013 | Weiman |
| 8,403,990 B2 | 3/2013 | Dryer et al. |
| 8,435,298 B2 | 5/2013 | Weiman |
| 8,491,659 B2 | 7/2013 | Weiman |
| 8,506,629 B2 | 8/2013 | Weiland |
| 8,518,120 B2 | 8/2013 | Glerum et al. |
| 8,523,944 B2 | 9/2013 | Jimenez et al. |
| 8,545,566 B2 | 10/2013 | Niemiec |
| 8,556,979 B2 | 10/2013 | Glerum et al. |
| 8,568,481 B2 | 10/2013 | Olmos |
| 8,628,577 B1 | 1/2014 | Jimenez |
| 8,628,578 B2 | 1/2014 | Miller et al. |
| 8,632,595 B2 | 1/2014 | Weiman |

(Continued)

*Primary Examiner* — Jan Christopher Merene
*Assistant Examiner* — Atiya Mahmud

(57) ABSTRACT

A spinal implant comprises a first member and a second member. A rotatable element defines an axis and is engageable to rotate the members about the axis. An actuator is rotatable for translating a part thereof to move the members between a first, contracted configuration and a second, expanded configuration. Systems and methods of use are disclosed.

19 Claims, 8 Drawing Sheets

(56) References Cited

U.S. PATENT DOCUMENTS

| | | |
|---|---|---|
| 8,663,329 B2 | 3/2014 | Ernst |
| 8,679,183 B2 | 3/2014 | Glerum et al. |
| 8,685,098 B2 | 4/2014 | Glerum et al. |
| 8,709,086 B2 | 4/2014 | Glerum et al. |
| 8,778,025 B2 | 7/2014 | Ragab et al. |
| 8,795,366 B2 | 8/2014 | Varela |
| 8,888,853 B2 | 11/2014 | Glerum et al. |
| 8,888,854 B2 | 11/2014 | Glerum et al. |
| 8,894,711 B2 | 11/2014 | Varela |
| 8,894,712 B2 | 11/2014 | Varela |
| 8,926,704 B2 | 1/2015 | Glerum |
| 8,940,049 B1 | 1/2015 | Jimenez |
| 9,039,771 B2 | 5/2015 | Glerum et al. |
| 9,119,730 B2 | 9/2015 | Glerum et al. |
| 9,427,331 B2 * | 8/2016 | Arnin ............ A61F 2/447 |
| 2004/0153065 A1 * | 8/2004 | Lim ............ A61F 2/442 606/53 |
| 2007/0255415 A1 * | 11/2007 | Edie ............ A61F 2/44 623/17.16 |
| 2008/0091211 A1 * | 4/2008 | Gately ............ A61F 2/4465 606/99 |
| 2009/0276049 A1 * | 11/2009 | Weiland ............ A61F 2/4465 623/17.16 |
| 2011/0054621 A1 | 3/2011 | Lim |
| 2011/0172774 A1 | 7/2011 | Varela |
| 2012/0010717 A1 * | 1/2012 | Spann ............ A61B 17/02 623/17.16 |
| 2012/0035729 A1 | 2/2012 | Glerum et al. |
| 2012/0109319 A1 | 5/2012 | Perisic |
| 2012/0150304 A1 | 6/2012 | Glerum et al. |
| 2012/0150305 A1 | 6/2012 | Glerum et al. |
| 2012/0158146 A1 | 6/2012 | Glerum et al. |
| 2012/0158147 A1 | 6/2012 | Glerum et al. |
| 2012/0158148 A1 | 6/2012 | Glerum et al. |
| 2013/0110241 A1 * | 5/2013 | Palmatier ............ A61F 2/4611 623/17.16 |
| 2013/0144388 A1 | 6/2013 | Emery et al. |
| 2013/0158664 A1 | 6/2013 | Palmatier et al. |
| 2013/0158668 A1 * | 6/2013 | Nichols ............ A61F 2/4611 623/17.16 |
| 2013/0268077 A1 * | 10/2013 | You ............ A61F 2/4455 623/17.16 |
| 2014/0121774 A1 | 5/2014 | Glerum et al. |
| 2014/0249628 A1 * | 9/2014 | Weiman ............ A61F 2/442 623/17.15 |
| 2014/0316522 A1 * | 10/2014 | Weiman ............ A61F 2/4455 623/17.16 |
| 2014/0324171 A1 | 10/2014 | Glerum et al. |
| 2014/0343678 A1 * | 11/2014 | Suddaby ............ A61F 2/46 623/17.16 |
| 2015/0351925 A1 * | 12/2015 | Emerick ............ A61F 2/447 623/17.16 |
| 2016/0089247 A1 * | 3/2016 | Nichols ............ A61F 2/30767 623/17.16 |

* cited by examiner

SPINAL IMPLANT SYSTEM AND METHOD

TECHNICAL FIELD

The present disclosure generally relates to medical devices for the treatment of musculoskeletal disorders, and more particularly to a surgical system that includes a spinal implant and a method for treating a spine.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility.

Non-surgical treatments, such as medication, rehabilitation and exercise can be effective, however, may fail to relieve the symptoms associated with these disorders. Surgical treatment of these spinal disorders includes fusion, fixation, correction, discectomy, laminectomy and implantable prosthetics. As part of these surgical treatments, spinal constructs, such as, for example, bone fasteners, spinal rods and interbody devices can be used to provide stability to a treated region. For example, during surgical treatment, surgical instruments can be used to deliver components of the spinal constructs to the surgical site for fixation with bone to immobilize a joint. This disclosure describes an improvement over these prior art technologies.

SUMMARY

In one embodiment, a spinal implant is provided. The spinal implant comprises a first member and a second member. A rotatable element defines an axis and is engageable to rotate the members about the axis. An actuator is rotatable for translating a part thereof to move the members between a first, contracted configuration and a second, expanded configuration. In some embodiments, systems and methods are disclosed.

BRIEF DESCRIPTION OF THE DRAWINGS

The present disclosure will become more readily apparent from the specific description accompanied by the following drawings, in which.

DETAILED DESCRIPTION

Figure 1:
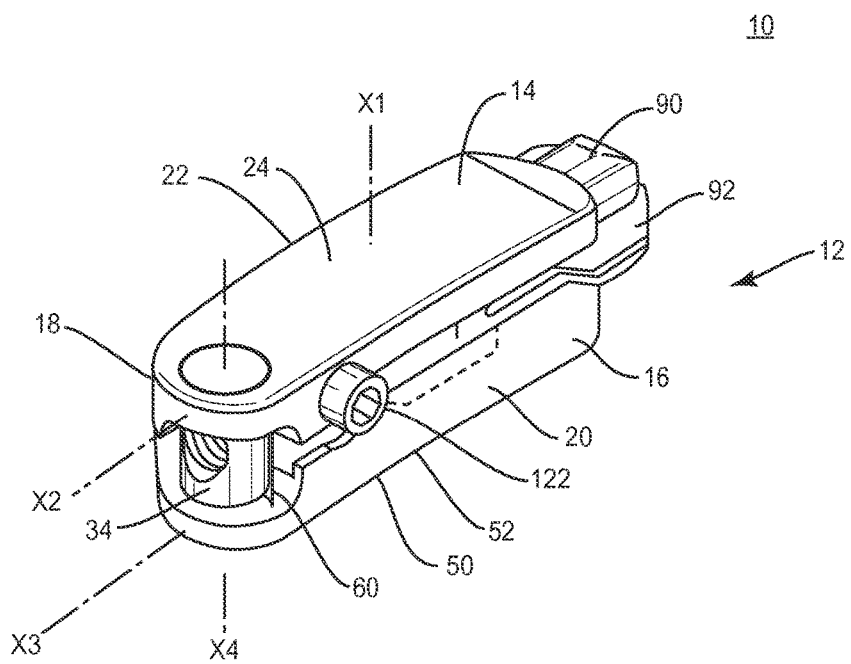
FIG. 1 is a perspective view, in part phantom, of components of one embodiment of a spinal implant system in accordance with the principles of the present disclosure.
Figure 2:
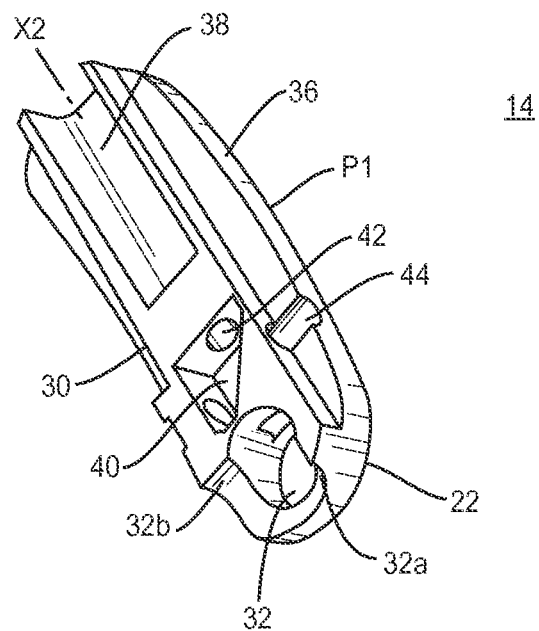
FIG. 2 is a perspective view of a component of the spinal implant system shown in FIG. 1.

The exemplary embodiments of the surgical system and related methods of use disclosed are discussed in terms of medical devices for the treatment of musculoskeletal disorders and more particularly, in terms of a surgical system that includes a spinal implant and a method for treating a spine.

In one embodiment, the present system includes a spinal implant including a steerable expandable interbody spacer. In one embodiment, the spinal implant includes a steerable expandable interbody spacer for anterior placement via a posterior approach. In one embodiment, the spinal implant includes a steerable expandable interbody spacer having a gearing mechanism and an actuation mechanism.

In some embodiments, the spinal implant includes a steerable expandable interbody spacer that is employed with a method for treating a spine, which includes the step of interbody placement from a midline trajectory. In some embodiments, the steerable interbody spacer is an interbody implant and the method includes a step such that the interbody implant is steerable for anterior placement. In some embodiments, the method includes the step of expanding the interbody implant to distract vertebrae. In some embodiments, the method includes the step of locking the interbody implant in position.

In some embodiments, the spinal implant includes an interbody implant that includes an interbody spacer that is steerable and can be expanded. In some embodiments, the interbody spacer is steered through a threaded pin contained within the interbody spacer and can freely rotate. In some embodiments, the interbody spacer is employed with an inserter that includes a threaded first shaft that engages the threaded pin inside the interbody spacer. In some embodiments, the connection of the interbody spacer with the inserter allows the interbody spacer to rotate, beginning on an axis with the inserter for introduction into the disc space. In some embodiments, the connection of the interbody spacer with the inserter in alignment with the axis disposes the interbody spacer in an orientation for introduction into the disc space. In some embodiments, the connection of the interbody spacer with the inserter includes a pivot point for rotation and/or an articulation axis that is disposed within the interbody spacer. In some embodiments, the interbody spacer can be rotated up to or beyond 90 degrees relative to the axis. In some embodiments, the interbody spacer can be rotated for orientation with an anterior portion of vertebrae.

In some embodiments, the interbody spacer is rotated up to or beyond 90 degrees relative to the axis and an expanding portion of the interbody spacer is actuated by a second shaft positioned parallel to the first shaft. In some embodiments, a tip of the second shaft engages and drives a first gear within the interbody spacer. In some embodiments, the first gear transmits torque from the second shaft to a second gear, and its axis is rotated 90 degrees from the first gear. In some embodiments, the second gear is connected to a threaded shaft that drives a wedge with ramps into the interbody spacer to facilitate expansion of the interbody spacer.

In some embodiments, the interbody spacer is employed with a method for treating a spine, which includes a lumbar interbody fusion performed through a midline access approach, for example, a posterior lumbar interbody fusion (PLIF trajectory). In some embodiments, the method includes the step of anterior graft placement. In some embodiments, the interbody spacer is easily operated and articulates to a 90 degree angle or greater, and expands. In some embodiments, this configuration allows an anterior implant placement, such as, for example, a Harms/Varga placement. In some embodiments, the interbody spacer expand to distract vertebrae and restore lordosis to lock the interbody spacer into position with vertebrae.

In some embodiments, the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. In some embodiments, the present disclosure may be employed with other osteal and bone related applications, including those associated with diagnostics and therapeutics. In some embodiments, the disclosed spinal implant system may be alternatively employed in a surgical treatment with a patient in a prone or supine position, and/or employ various surgical approaches to the spine, including anterior, posterior, posterior mid-line, direct lateral, postero-lateral, and/or antero lateral approaches, and in other body regions. The present disclosure may also be alternatively employed with procedures for treating the lumbar, cervical, thoracic, sacral and pelvic regions of a spinal column. The spinal implant system of the present disclosure may also be used on animals, bone models and other non-living substrates, such as, for example, in training, testing and demonstration.

The present disclosure may be understood more readily by reference to the following detailed description of the embodiments taken in connection with the accompanying drawing figures, which form a part of this disclosure. It is to be understood that this application is not limited to the specific devices, methods, conditions or parameters described and/or shown herein, and that the terminology used herein is for the purpose of describing particular embodiments by way of example only and is not intended to be limiting. In some embodiments, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

As used in the specification and including the appended claims, "treating" or "treatment" of a disease or condition refers to performing a procedure that may include administering one or more drugs to a patient (human, normal or otherwise or other mammal), employing implantable devices, and/or employing instruments that treat the disease, such as, for example, micro-discectomy instruments used to remove portions bulging or herniated discs and/or bone spurs, in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

The following discussion includes a description of a surgical system including one or more spinal implants, related components and methods of employing the surgical system in accordance with the principles of the present disclosure. Alternate embodiments are disclosed. Reference is made in detail to the exemplary embodiments of the present disclosure, which are illustrated in the accompanying figures. Turning to FIGS. 1-7, there are illustrated components of a surgical system, such as, for example, a spinal implant system 10 including a spinal implant, such as, for example, an interbody spacer 12.

The components of spinal implant system 10 can be fabricated from biologically acceptable materials suitable for medical applications, including metals, synthetic polymers, ceramics and bone material and/or their composites. For example, the components of spinal implant system 10, individually or collectively, can be fabricated from materials such as stainless steel alloys, commercially pure titanium, titanium alloys, Grade 5 titanium, super-elastic titanium alloys, cobalt-chrome alloys, stainless steel alloys, super-elastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO$_4$ polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations.

Various components of spinal implant system 10 may have material composites, including the above materials, to achieve various desired characteristics such as strength, rigidity, elasticity, compliance, biomechanical performance, durability and radiolucency or imaging preference. The components of spinal implant system 10, individually or collectively, may also be fabricated from a heterogeneous material such as a combination of two or more of the above-described materials. The components of spinal implant system 10 may be monolithically formed, integrally connected or include fastening elements and/or instruments, as described herein.

Spinal implant system 10 is employed, for example, with a minimally invasive procedure, including percutaneous techniques, mini-open and open surgical techniques to deliver and introduce instrumentation and/or one or more spinal implants, such as, for example, interbody spacer 12, at a surgical site within a body of a patient, for example, a section of a spine. In some embodiments, spinal implant system 10 may be employed with surgical procedures, as described herein, and/or, for example, surgical procedures including corpectomy, discectomy, fusion and/or fixation treatments that employ spinal implants to restore the mechanical support function of vertebrae.

Interbody spacer 12 includes a member 14 and a member 16. Interbody spacer 12 defines an axis X1 and extends between an end, such as, for example, an anterior end 18 and an end, such as, for example, a posterior end 20.

Member 14 defines a longitudinal axis X2 disposed substantially perpendicular to axis X1. Member 14 includes a surface 22 that defines a vertebral engaging surface 24. In some embodiments, the cross-sectional geometry of member 14 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 24 may be smooth, even, rough, textured, porous, semi-porous, dimpled and/or polished.

Member 14 includes a surface 30 that defines a cavity 32 configured for disposal of a rotatable element, such, as for example, a pin 34, as described herein. Member 14 is configured for relative rotation about pin 34. Surface 30 includes an end surface, such as, for example, a stop 32a and an end surface, such as, for example, a stop 32b. Stops 32a, 32b are disposed about cavity 32 and configured to limit an angular range of relative rotation of members 14, 16 about pin 34, as described herein. Member 14 includes a surface 36 that defines a perimeter P1 of member 14 disposed about the body of member 14. In some embodiments, perimeter P1 has an oblong and/or elliptical configuration. Pin 34 is disposable with cavity 32 and within the boundary of perimeter P1.

Surface 30 defines a cavity 38 and a cavity 40. Cavity 38 is configured for moveable disposal of an actuator 90, as described herein. Cavity 40 is configured for rotatable disposal of an actuator 90, as described herein. An opening 42 communicates with cavities 38, 40 and is configured for disposal of a shaft 110, as described herein. Surface 36 defines an opening 44 in communication with cavity 40. Opening 44 is configured for rotatable disposal of a portion of a cam 122, as described herein. In some embodiments, surface 36 may be smooth, even, rough, textured, porous, semi-porous, dimpled and/or polished.

Member 16 defines a longitudinal axis X3 disposed substantially perpendicular to axis X1 and parallel to axis X2. Member 16 includes a surface 50 that defines a vertebral engaging surface 52. In some embodiments, the cross-sectional geometry of member 16 may have various configurations, such as, for example, round, oval, oblong, triangular, polygonal having planar or arcuate side portions, irregular, uniform, non-uniform, consistent, variable, horseshoe shape, U-shape or kidney bean shape. In some embodiments, surface 52 may be smooth, even, rough, textured, porous, semi-porous, dimpled and/or polished.

Member 16 includes a surface 54 that defines a cavity 56, in communication with cavity 32 and configured for disposal of pin 34, as described herein. Member 16 is configured for relative rotation about pin 34. Cavity 56 includes an end surface, such as, for example, a stop 56a and an end surface, such as, for example, a stop 56b. Stops 56a, 56b are disposed about cavity 56 and aligned with stops 32a, 32b. Stops 56a, 56b are configured to limit an angular range of relative rotation of members 14, 16 about pin 34, as described herein. Member 16 includes a surface 58 that defines a perimeter P2 of member 16 disposed about the body of member 16. In some embodiments, perimeter P2 has an oblong and/or elliptical configuration. Pin 34 is disposable with cavity 56 and within the boundary of perimeter P2. Cavities 34, 56 are aligned with assembled members 14, 16 and form a pivot joint 60 for disposal of pin 34, as shown in FIG. 1.

Surface 54 defines an engagement surface 70 configured to mate with a portion of actuator 90 for disposal of interbody spacer 12 in a first configuration, such as, for example, a contracted configuration and slidably engage actuator 90 for disposal of interbody spacer 12 in a second configuration, such as, for example, an expanded configuration, as described herein.

Figure 4:
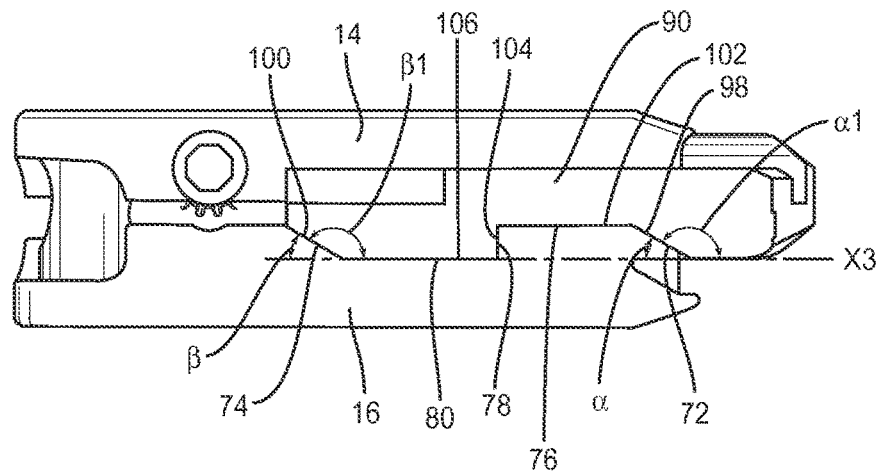
FIG. 4 is a side view of components of the spinal implant system shown in FIG. 1.

Engagement surface 70 includes a ramp 72 and a ramp 74, as shown in FIG. 4. Ramp 72 includes an angle of inclination α oriented relative to axis X3. Ramp 74 includes an angle of inclination β oriented relative to axis X3. In some embodiments, angle α is equal to angle β. In some embodiments, angle α is less than angle β. In some embodiments, angle α is greater than angle β. Ramp 72 is spaced apart from ramp 74 by planar surfaces 76, 78, 80. Member 16 includes a planar surface 82 disposed adjacent ramp 74. In one embodiment, surface 76 is connected with surface 78 at a substantially perpendicular angle. In one embodiment, surface 78 is connected with surface 80 at a substantially perpendicular angle.

Surfaces 76 and 82 are configured to mate with actuator 90 in an expanded configuration, as described herein. In some embodiments, surfaces 76, 78 and surfaces 78, 80 may be disposed at alternate angular orientations, such as, for example, acute or obtuse, and/or may be offset or staggered. In some embodiments, ramps 72, 74 and surfaces 76, 78, 80 are monolithically formed, connected by fastening elements or separate and distinct structure.

Figure 5:
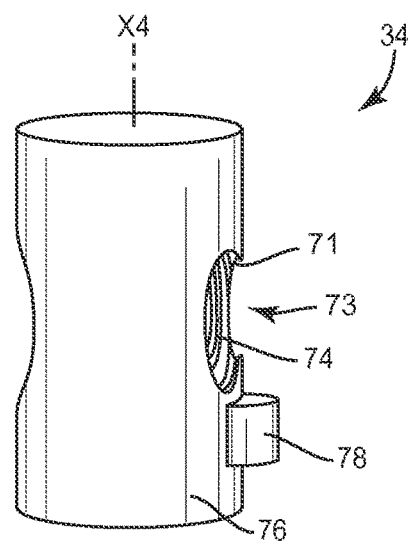
FIG. 5 is a perspective view of a component of the spinal implant system shown in FIG. 1.

Pin 34 has a cylindrical configuration, as shown in FIG. 5, and is oriented for disposal within cavities 32, 56 and pivot joint 60. Pin 34 defines an axis X4, offset from axis X1 along members 14, 16 and disposed within the perimeter of interbody spacer 12, which includes perimeters P1, P2. In some embodiments, the cross-sectional geometry of pin 34 may have various configurations, such as, for example, oval, oblong, triangular, polygonal having planar or arcuate side portions, irregular, uniform, non-uniform, consistent, or variable.

Pin 34 includes a surface 71 that defines a cavity 73. Surface 71 includes a threaded portion 74 configured for engagement with a surgical instrument, as described herein. In some embodiments, pin 34 includes an outer surface 76 that may be smooth, even, rough, textured, porous, semi-porous, dimpled and/or polished. Surface 76 defines a flange 78 disposed adjacent cavity 73. Flange 78 is configured engage stops 56*a*, 56*b* to limit rotation of members 14, 16 relative to pin 34. In some embodiments, flange 78 is engageable with stops 32*a*, 32*b* to limit rotation of members 14, 16 relative to pin 34.

Members 14, 16 are rotatable relative to pin 34 through an angular range, as describe herein. Members 14, 16 are selectively rotatable relative to pin 34 between stops 56*a*, 56*b*. Members 14, 16 articulate about axis X4, which is disposed within perimeters P1, P2 of interbody spacer 12. In some embodiments, members 14, 16 are rotatable relative to pin 34 through an angular range of 0-100 degrees. In some embodiments, members 14, 16 are passively rotatable relative to pin 34 such that manipulation of a surgical inserter connected with interbody spacer 12 during insertion of interbody spacer 12 with a vertebral space causes members 14, 16 to rotate relative to pin 34 due to engagement and resistance of tissue. In some embodiments, members 14, 16 are selectively rotatable relative to pin 34 between stops 32*a*, 32*b*.

Figure 6:
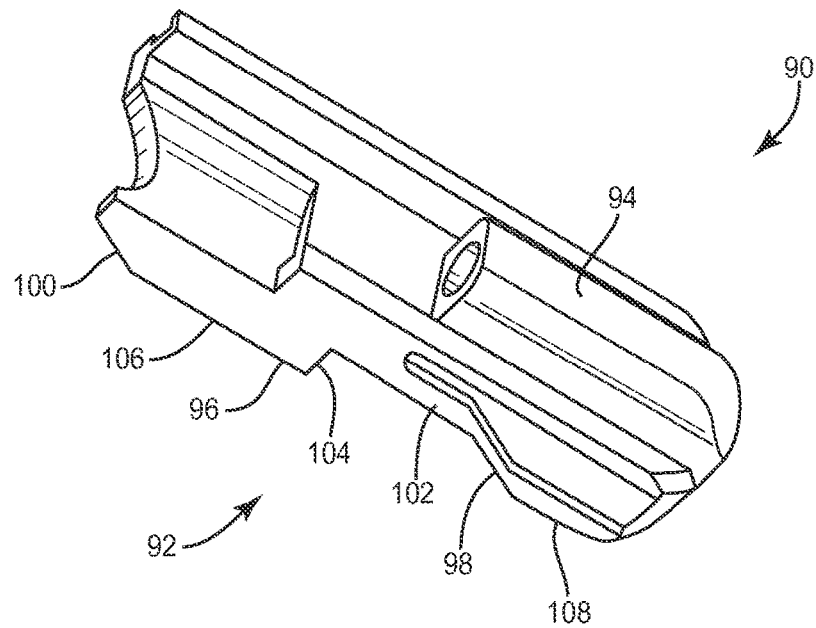
FIG. 6 is a perspective view of a component of the spinal implant system shown in FIG. 1.

Actuator 90 is disposed in an intermediate orientation with members 14, 16. Actuator 90 includes a wedge 92 and a housing 94, as shown in FIG. 6. Wedge 92 includes a surface 96 that is configured to engage surface 70 of member 16. Surface 96 includes a ramp 98 and a ramp 100. Ramp 98 includes an angle of inclination α1 relative to axis X3, as shown in FIG. 4. Ramp 100 includes an angle of inclination β1 relative to axis X3, as shown in FIG. 4.

In some embodiments, angle α1 is equal to angle β1. In some embodiments, angle α1 is less than angle β1. In some embodiments, angle α1 is greater than angle β1. Ramp 98 is spaced apart from ramp 100 by planar surfaces 102, 104, 106. Wedge 92 includes a planar surface 108 disposed adjacent ramp 98. In one embodiment, surface 102 is connected with surface 104 at a substantially perpendicular angle. In one embodiment, surface 104 is connected with surface 106 at a substantially perpendicular angle. In some embodiments, surfaces 100, 102, 104 may be disposed at alternate angular orientations, such as, for example, acute or obtuse, and/or may be offset or staggered. In some embodiments, ramps 98, 100 and surfaces 102, 104, 106 are monolithically formed, connected by fastening elements or separate and distinct structure.

Ramps 98, 100 and surfaces 102, 104, 106 movably engage member 16 to expand and collapse interbody spacer 12 between a contracted configuration, such that the surfaces of members 14, 16 are disposed in a nested mating engagement and an expanded configuration of members 14, 16, as described herein.

Actuator 90 includes a shaft 110. Shaft 110 extends parallel to axes X2, X3. Shaft 110 is configured to rotate within housing 94 to facilitate expansion and contraction of members 14, 16. Shaft 110 includes a part 114 and a part 116 disposed in a telescoping configuration such that as actuator 90 translates, part 116 translates within part 114 via threaded engagement. As part 116 is rotated, part 114 translates relative to part 116 via the threaded engagement within part 114. Relative translation of parts 114, 116 translates the ramp surfaces described herein for engagement therebetween to facilitate expansion and contraction of interbody spacer 12, as described herein. Part 116 includes a bevel gear 120 configured for engagement with cam 122.

Cam 122 includes an instrument engagement portion 124 and a shaft 126 having a bevel gear 126. Cam 122 is rotatable within opening 44 such that gear 126 engages gear 120 to cause axial translation of shaft 110. Instrument engagement portion 124 includes a socket 128 having a hexagonal configuration. In some embodiments, socket 128 has a cruciform, phillips, square, hexagonal, polygonal, star cross sectional configuration configured for disposal of a correspondingly shaped portion of a driver. Socket 128 is configured for engagement with a surgical instrument, as described herein.

Rotation of shaft 110 causes axial translation of actuator 90 such that wedge 92 and housing 94 are movable relative to members 14, 16 to expand and collapse interbody spacer 12. Socket 128 is engaged with a surgical instrument, as described herein, to facilitate actuation of the component parts of interbody spacer 12 and disposal thereof in various configurations.

Figure 8:
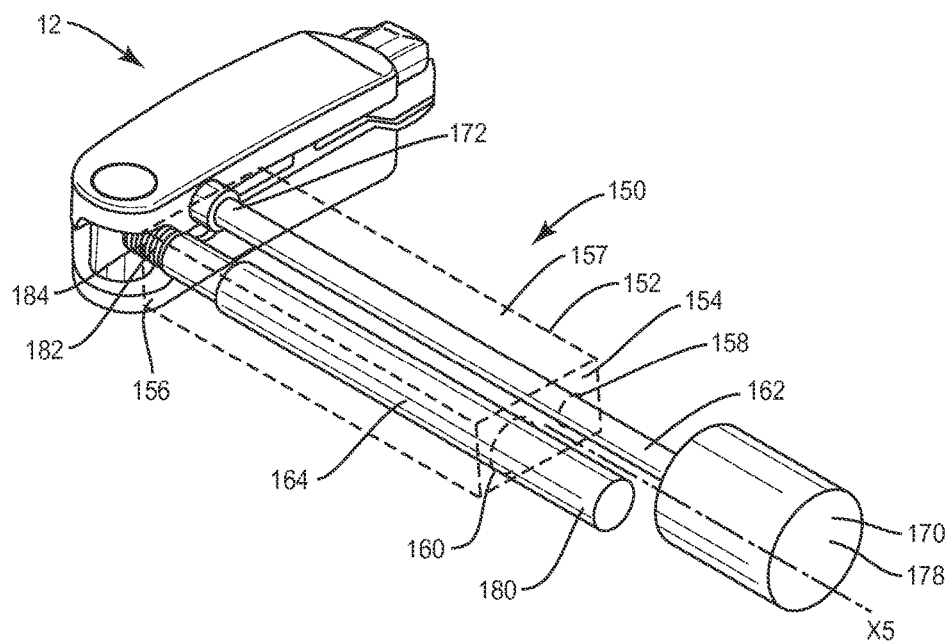
FIG. 8 is a perspective view, in part phantom, of components of one embodiment of a spinal implant system in accordance with the principles of the present disclosure.

An instrument 150 includes a body 152 that extends between an end 154 and an end 156 to define an axis X5, as shown in FIG. 8. Body 152 includes a sleeve 157. Sleeve 157 includes a surface, such as, for example, a channel 158 and a surface, such as, for example, a channel 160. Channel 158 is configured for disposal of at least a portion of a member, such as, for example, a driver 162. Channel 160 is configured for disposal of at least a portion of a member, such as, for example, a shaft 164.

Figure 9:
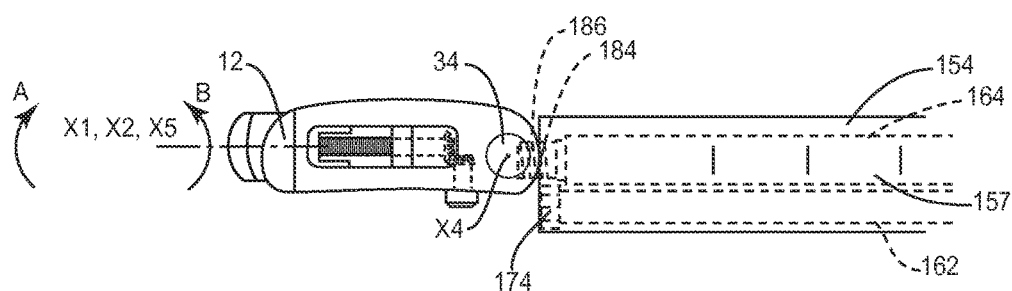
FIG. 9 is a side break away view, in part phantom, of the components shown in FIG. 8.

Driver 162 extends between an end 170 and an end 172. End 172 includes an engagement portion 174 configured to engage cam 122, as shown in FIG. 9. In some embodiments, engagement portion 174 includes configurations, such as, for example, triangular, square, polygonal, hexalobular, star or torx. End 170 includes a rotatable handle 178 configured to rotate driver 162 such that cam 122 actuates translation of actuator 90.

Shaft 164 extends between an end 180 and an end 182. End 182 includes a threaded portion 184 configured for engagement with pin 34, as described herein. End 180 includes a handle configured to facilitate manipulation of shaft 164. Threaded portion 184 is configured to engage pin 34 and to actuate rotation of members 14, 16 relative to pin 34. Threaded portion 184 includes an end thread, such as, for example, tooth 186 configured for engagement with surfaces 36, 58 to provisionally lock members 14, 16 to prevent rotation and stabilize instrument 150 with interbody spacer 12. In some embodiments, release of tooth 186 from surfaces 36, 58 allows for selective passive rotation of members 14, 16 relative to pin 34.

Referring to FIGS. 9-14, in assembly, operation and use, spinal implant system 10 including interbody spacer 12, similar to the systems and methods described herein, is employed with a surgical procedure, such as, for example, a lumbar interbody fusion performed through a midline access approach, for example, a PLIF trajectory for treatment of a spine of a patient including vertebrae V. Spinal implant system 10 may also be employed with other surgical procedures, such as, for example, discectomy, laminectomy, fusion, laminotomy, laminectomy, nerve root retraction, foramenotomy, facetectomy, decompression, spinal nucleus or disc replacement.

Spinal implant system 10 is employed with a lumbar interbody fusion including surgical arthrodesis to immobilize a joint for treatment of an applicable condition or injury of an affected section of a spinal column and adjacent areas within a body. For example, vertebrae V includes a vertebra V1 and a vertebra V2. In some embodiments, vertebrae V1, V2 include diseased and/or damaged vertebra and intervertebral discs. In some embodiments, components of spinal implant system 10 are configured for insertion with a vertebral space between vertebrae V1, V2 to space apart articular joint surfaces, provide support and maximize stabilization of vertebrae V.

In use, to treat the affected section of vertebrae V, a medical practitioner obtains access to a surgical site including vertebrae V in any appropriate manner, such as through incision and retraction of tissues. In some embodiments, spinal implant system 10 may be used in any existing surgical method or technique including open surgery, mini-open surgery, minimally invasive surgery and percutaneous surgical implantation, whereby vertebrae V is accessed through a mini-incision, or sleeve that provides a protected passageway and/or surgical pathway to the area. Once access to the surgical site is obtained, a surgical procedure, as described herein, is performed for treating the spine disorder. The diseased and/or damaged portion of vertebrae V, which may include diseased and/or damaged intervertebral discs, are removed to create a vertebral space between vertebrae V1, V2.

A preparation instrument (not shown) is employed to remove disc tissue, fluids, adjacent tissues and/or bone, and scrape and/or remove tissue from endplate surfaces E1 of vertebra V1 and/or endplate surface E2 of vertebra V2. In some embodiments, the size of interbody implant 12 is selected after trialing. In some embodiments, interbody spacer 12 is visualized by fluoroscopy and oriented before introduction into the vertebral space.

Interbody spacer 12 is provided in a contracted orientation, as shown for example in FIG. 1, such that ramps 72, 74 are engaged with ramps 98, 100 and surfaces 76, 78, 80 are mated with surfaces 102, 104, 106, as shown in FIG. 4. Surgical instrument 150 is connected with interbody spacer 12 for disposal in an introduction or delivery orientation, as shown in FIG. 9, for alignment of interbody spacer 12 with the surgical pathway such that interbody spacer 12 is steerable to the vertebral space between vertebrae V1, V2. Shaft 164 is connected with pin 34 such that threaded portion 184 is engaged with threaded portion 74 and axes X1, X2 and X5 are disposed in parallel alignment. As shaft 164 is rotated, in the direction shown by arrow A in FIG. 9, tooth 186 engages surfaces 36, 58 to provisionally lock instrument 150 with interbody spacer 12.

Figure 10:
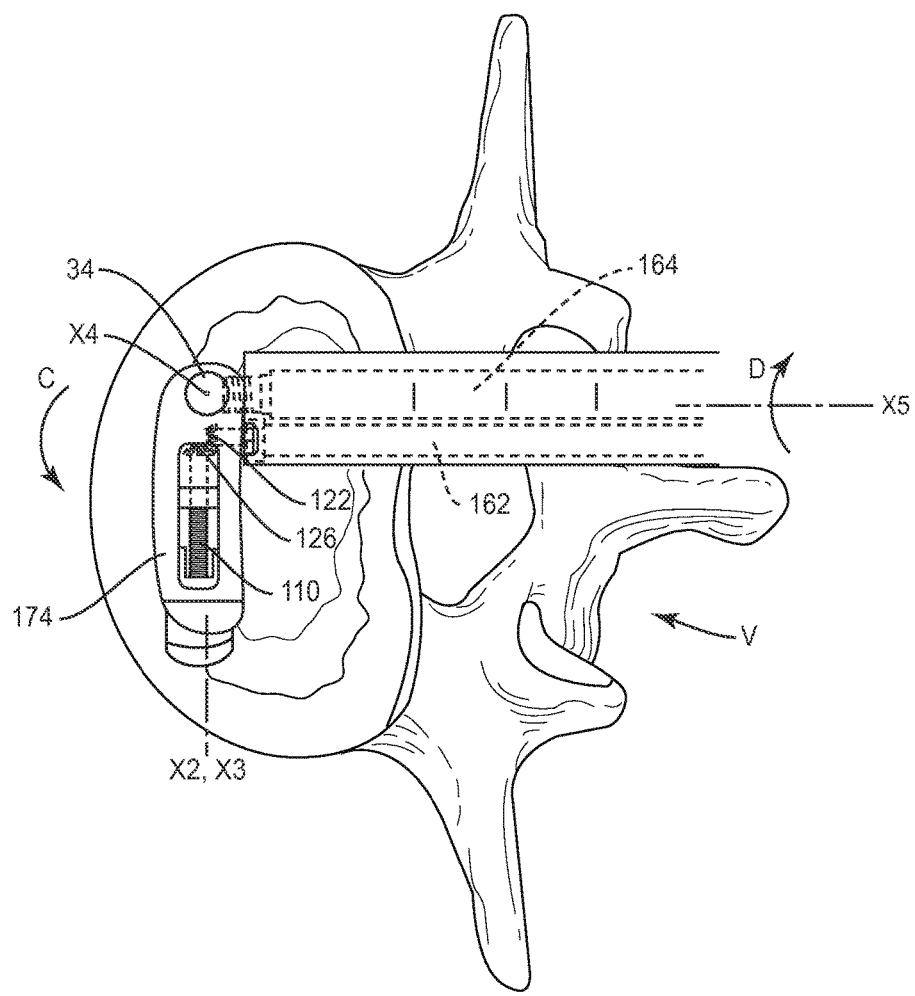
FIG. 10 is a break away plan view, in part phantom, of the components shown in FIG. 8 disposed with vertebrae.
Figure 11:
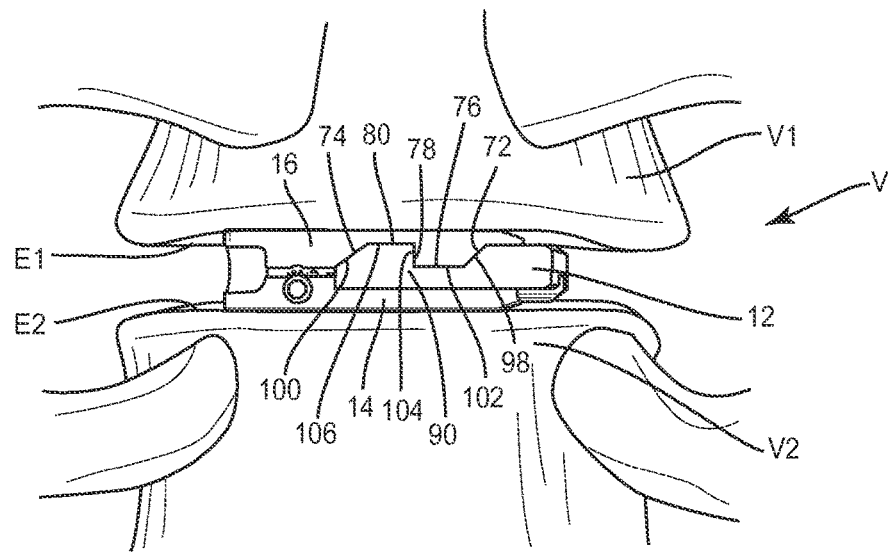
FIG. 11 is a plan view of components of the spinal implant system shown in FIG. 8 disposed with vertebrae.
Figure 12:
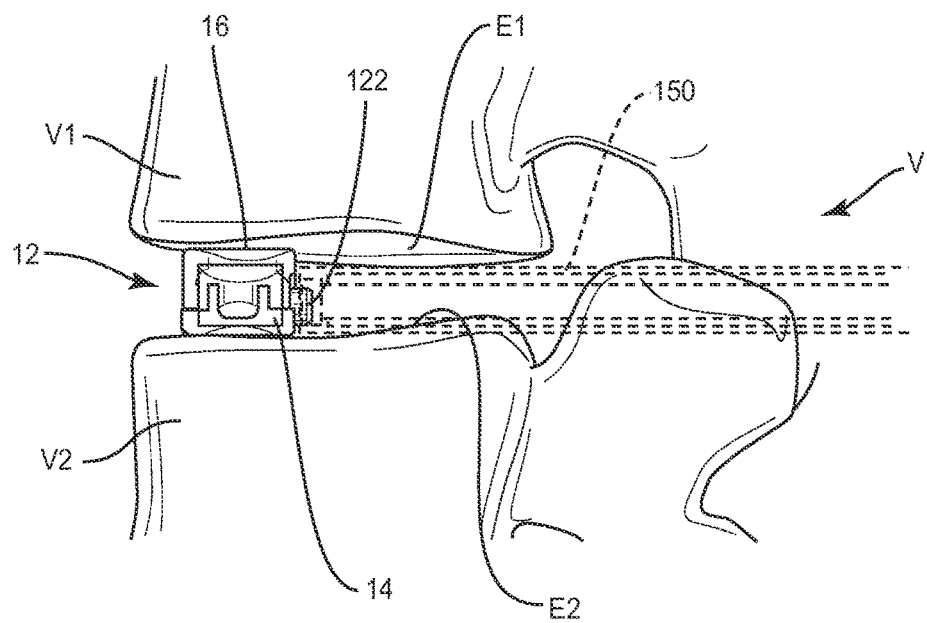
FIG. 12 is a plan view, in part phantom, of components of the spinal implant system shown in FIG. 8 disposed with vertebrae.

Shaft 164 is rotated, in a direction shown by arrow B, to disengage tooth from surfaces 36, 58 to allow interbody spacer 12 to rotate relative to pin 34 about axis X4. Surgical instrument 150 is manipulated along the surgical pathway to deliver interbody spacer 12 to the vertebral space between vertebrae V1, V2, as shown in FIG. 10. Manipulation of surgical instrument 150 passively rotates and/or steers interbody spacer 12, in a direction shown by arrow C, within the angular range provided by stops 32a, 32b and/or 56a, 56b, as described herein, into a selected position with the vertebral space between vertebrae V1, V2. In some embodiments, rotation of members 14, 16 relative to pin 34 is limited by engagement of shaft 164 with stops 32a, 32b and engagement of flange 78 with stops 56a, 56b. Interbody spacer 12 is selectively positioned to an implantable orientation adjacent an anterior portion of the vertebral space between vertebrae V1, V2 such that axes X2, X3 approach a substantially perpendicular orientation relative to axis X5, as shown in FIGS. 10-12.

Figure 13:
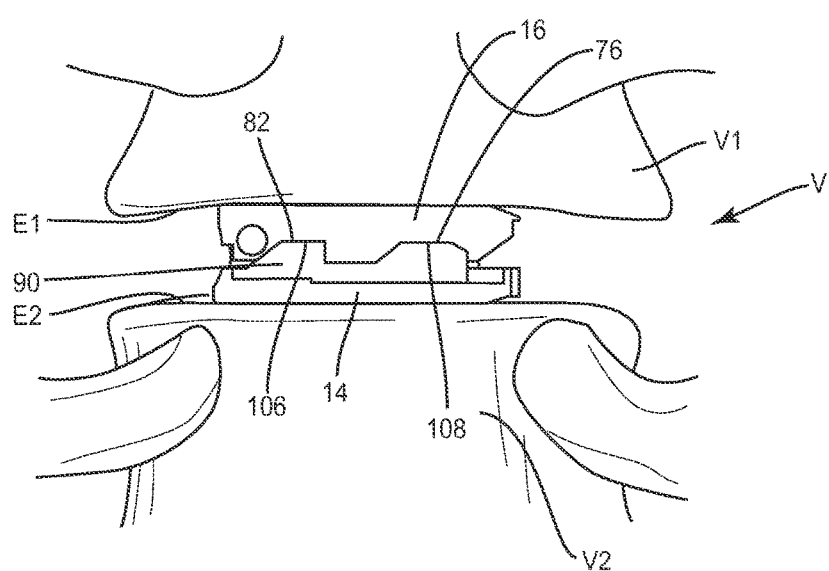
FIG. 13 is a plan view of components of the spinal implant system shown in FIG. 8 disposed with vertebrae.
Figure 14:
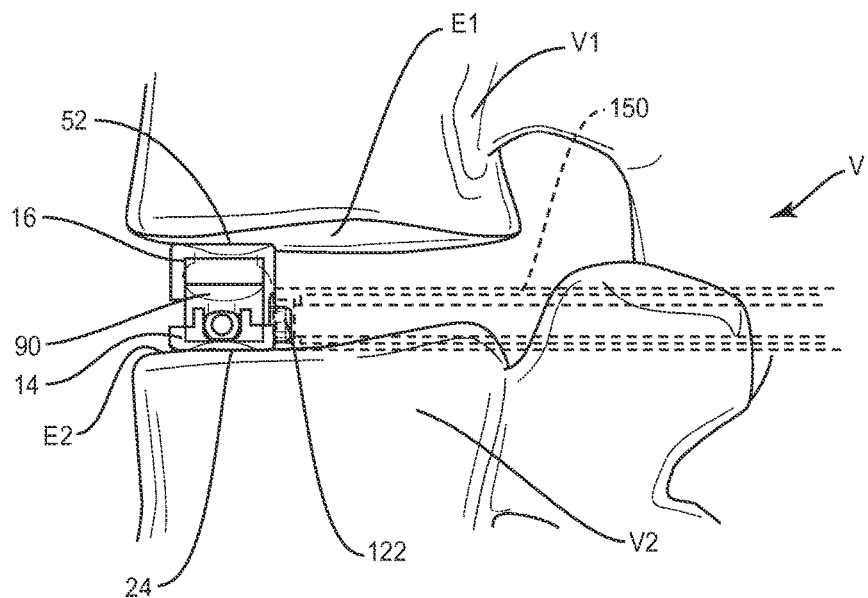
FIG. 14 is a plan view, in part phantom, of components of the spinal implant system shown in FIG. 8 disposed with vertebrae.

Driver 162 is engaged with cam 122 such that portion 174 engages socket 128. Driver 162 is rotated, in the direction shown by arrow D in FIG. 10, to expand interbody spacer 12 from the contracted configuration. Rotation of driver 162 causes gear 126 to rotatably engage gear 120. Part 114 translates relative to part 116, as described herein, such that ramps 72, 74 translate relative to ramps 98, 100 and surfaces 76, 78, 80 translate relative to surfaces 102, 104, 106. The angled surfaces of ramps 72, 74 and 98, 100 engage to space apart members 14, 16 and dispose interbody spacer 12 in an expanded configuration, as shown in FIGS. 13 and 14. Members 14, 16 are expanded to engage adjacent vertebral endplates E1, E2, such that surface 52 engages endplate E1 and surface 24 engages endplate E2 to restore vertebral spacing and provide distraction and/or restore mechanical support function. Surgical instrument 150 is disengaged from interbody spacer 12 such that driver 162 is removed from cam 122 and shaft 164 is threadably disengaged from pin 34.

In some embodiments, interbody spacer 12 provides a footprint that improves stability and decreases the risk of subsidence into tissue. In some embodiments, interbody spacer 12 provides height restoration between vertebral bodies, decompression, restoration of sagittal and/or coronal balance and/or resistance of subsidence into vertebral endplates.

In some embodiments, interbody spacer 12 engages and spaces apart opposing endplate surfaces E1, E2 and is secured within a vertebral space to stabilize and immobilize portions of vertebrae V in connection with bone growth for fusion and fixation of vertebrae V1, V2. Fixation of interbody spacer 12 with endplate surfaces E1, E2 may be facilitated by the resistance provided by the joint space and/or engagement with endplate surfaces E1, E2.

In some embodiments, interbody spacer 12 may engage only one endplate. Components of spinal implant system 10 including interbody spacer 12 can be delivered or implanted as a pre-assembled device or can be assembled in situ. Components of spinal implant system 10 including interbody spacer 12 may be completely or partially revised, removed or replaced in situ. In some embodiments, one or all of the components of spinal implant system 10 can be delivered to the surgical site via mechanical manipulation and/or a free hand technique.

In one embodiment, spinal implant system 10 includes a plurality of interbody spacers 12. In some embodiments, employing a plurality of interbody spacers 12 can optimize the amount of vertebral space that can be spaced apart such that the joint spacing dimension can be preselected. The plurality of interbody spacers 12 can be oriented in a side by side engagement, spaced apart and/or staggered.

In some embodiments, spinal implant system 10 includes an agent, which may be disposed, packed, coated or layered within, on or about the components and/or surfaces of spinal implant system 10. In some embodiments, the agent may include bone growth promoting material, such as, for example, bone graft to enhance fixation of interbody spacer 12 with vertebrae. In some embodiments, the agent may include one or a plurality of therapeutic agents and/or pharmacological agents for release, including sustained release, to treat, for example, pain, inflammation and degeneration.

In one embodiment, interbody spacer 12 may include fastening elements, which may include locking structure, configured for fixation with vertebrae V1, V2 to secure joint surfaces and provide complementary stabilization and immobilization to a vertebral region. In some embodiments, locking structure may include fastening elements such as, for example, rods, plates, clips, hooks, adhesives and/or flanges. In some embodiments, the components of spinal implant system 10 can be used with screws to enhance fixation. The components of spinal implant system 10 can be made of radiolucent materials such as polymers. Radiomarkers may be included for identification under x-ray, fluoroscopy, CT or other imaging techniques.

In some embodiments, the use of microsurgical and image guided technologies may be employed to access, view and repair spinal deterioration or damage, with the aid of spinal implant system 10. Upon completion of the procedure, the non-implanted components, surgical instruments and assemblies of spinal implant system 10 are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. A spinal implant comprising:
a first member;
a second member;
a rotatable element defining an axis and being engageable to rotate the members about the axis;
a cam extending through an opening in the first member; and
an actuator that is spaced completely apart from the rotatable element, the actuator comprising a first part and a second part disposed in a telescoping configuration with the first part, the actuator including a housing having a wedge that axially translates relative to the members and includes spaced ramps, the first part being fixed to the housing, the second part engaging the cam, the second part being rotatable relative to the first part to translate the first part relative to the second part to move the members between a first, contracted configuration and a second, expanded configuration.

2. A spinal implant as recited in claim 1, wherein each of the members define a perimeter and the rotatable element is disposed within the perimeter of each member.

3. A spinal implant as recited in claim 1, wherein each of the members include an inner surface and the inner surfaces define a cavity configured for disposal of the rotatable element such that the rotatable element is movable relative to the members.

4. A spinal implant as recited in claim 1, wherein the rotatable element comprises a pin and the members are rotatable relative to the pin.

5. A spinal implant as recited in claim 1, wherein the rotatable element comprises a pin having an inner surface defining a cavity, the inner surface including a threaded portion.

6. A spinal implant as recited in claim 1, wherein the members are rotatable relative to the rotatable element through an angular range of 0-100 degrees.

7. A spinal implant as recited in claim 1, wherein the members are rotatable relative to the rotatable element through an angular range between a first stop of the members and a second stop of the members.

8. A spinal implant as recited in claim 1, wherein the members are passively rotatable relative to the rotatable element.

9. A spinal implant as recited in claim 1, wherein the second part includes a gear that engages a gear of the cam.

10. A spinal implant as recited in claim 1, wherein the second part includes a threaded shaft that engages a threaded inner surface of the first part.

11. A spinal implant as recited in claim 1, wherein the spaced ramps include a first ramp and a second ramp.

12. A spinal implant as recited in claim 1, wherein rotation of the second part relative to the first part translates the first part relative to the second part and the wedge relative to the members to move the members between the configurations.

13. A spinal implant system comprising:
an interbody implant comprising a first member, a second member, a rotatable element disposed with the members, a cam extending through an opening in the first member and an actuator that is completely spaced apart from the rotatable element, the actuator including a first part and a second part disposed in a telescoping configuration with the first part, the second part engaging the cam, the actuator including a housing having a wedge that axially translates relative to the members and includes spaced ramps, the first part being fixed to the housing; and
a surgical instrument comprising a first shaft engageable with the rotatable element to rotate the members relative thereto and a second shaft engageable with the cam to rotate the cam and the second part for translating the first part relative to the second part to move the members between a first, contracted configuration and a second, expanded configuration.

14. A spinal implant system as recited in claim 13, wherein the first shaft rotates the members relative to the rotatable element between a first orientation such that the interbody implant is axially aligned with the first shaft and a second orientation such that the interbody implant is disposed transverse to the first shaft.

15. A spinal implant system as recited in claim 13, wherein the first shaft is threaded with the rotatable element to rotate the members relative to the rotatable element through an angular range of 0-100 degrees.

16. A spinal implant system as recited in claim 13, wherein the first shaft is threaded with the rotatable element to passively rotate the members relative to the rotatable element.

17. A spinal implant system as recited in claim 13, wherein the shafts are disposed in a relative parallel orientation.

18. A spinal implant system as recited in claim 13, wherein the second part includes a gear that engages a gear of the cam, the second part having a threaded shaft that engages a threaded inner surface of the first part.

19. A spinal implant comprising:
a first member having a vertebral engaging surface;
a second member having a vertebral engaging surface, each of the members including an inner surface and the inner surfaces define a cavity;
a pin disposable in the cavity of the first member and second member and being engageable to rotate the members relative to the pin;
a cam extending through an opening in the first member; and
an actuator that is spaced apart from the pin, the actuator including first part and a second part disposed in a telescoping configuration with the first part, the second part having a gear that engages a gear of the cam, the actuator further including a housing having a wedge, the first part being fixed relative to the housing such that rotation of the second part relative to the first part translates the first part relative to the second part and the wedge relative to the members to move the members between a first, contracted configuration and a second, expanded configuration.

* * * * *

UNITED STATES PATENT AND TRADEMARK OFFICE
CERTIFICATE OF CORRECTION

PATENT NO. : 9,730,806 B2
APPLICATION NO. : 14/524989
DATED : August 15, 2017
INVENTOR(S) : Capote It is certified that error appears in the above-identified patent and that said Letters Patent is hereby corrected as shown below:

In the Drawings

Figure 3:
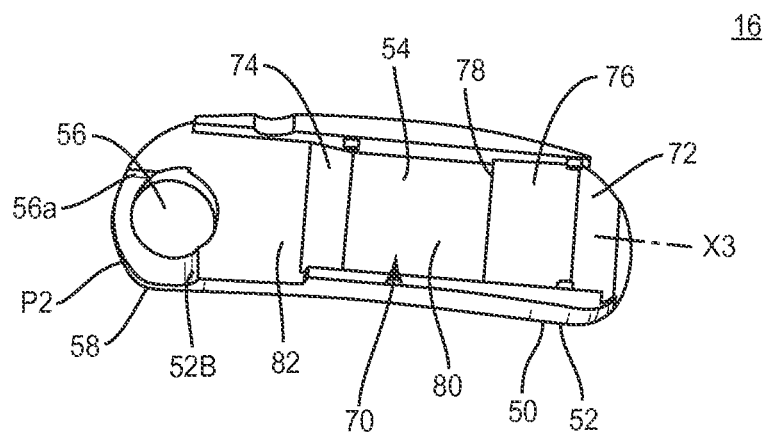
FIG. 3 is a perspective view of a component of the spinal implant system shown in FIG. 1.

In Fig. 3, Sheet 2 of 8, delete Tag "52B" and insert Tag -- 56b --, therefor.

In Fig. 5, Sheet 3 of 8, delete Tag "74" and insert Tag -- 75 --, therefor.

In Fig. 5, Sheet 3 of 8, delete Tag "76" and insert Tag -- 77 --, therefor.

In Fig. 5, Sheet 3 of 8, delete Tag "78" and insert Tag -- 79 --, therefor.

Figure 7:
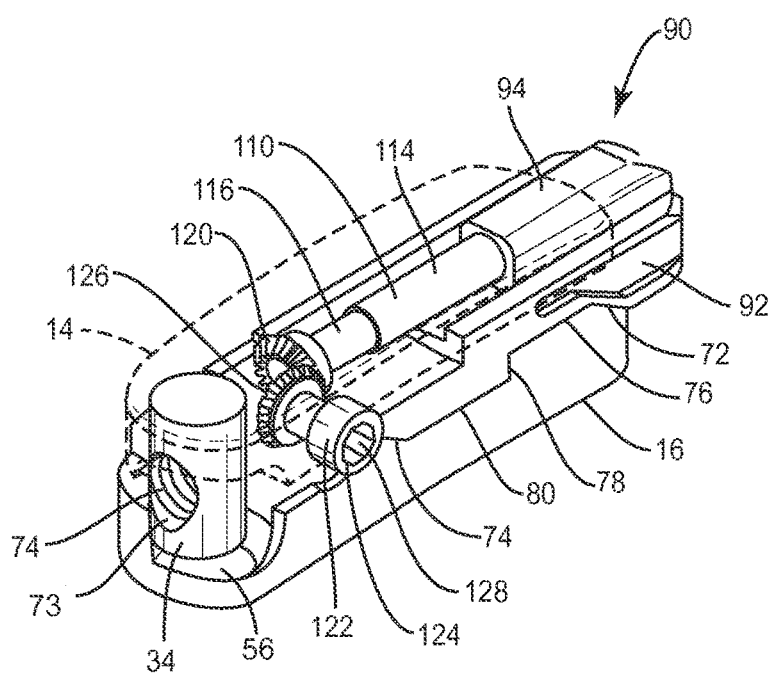
FIG. 7 is a perspective view, in part phantom, of components of the spinal implant system shown in FIG. 1.

In Fig. 7, Sheet 4 of 8, delete Tag "74" next to Tag "73" and insert Tag -- 75 --, therefor.

In the Specification

In Column 5, Line 7, delete "polyaetide," and insert -- polyketide, --, therefor.

In Column 5, Line 8, delete "polycaroplaetohe" and insert -- polycaprolactone --, therefor.

In Column 6, Line 30, delete "Cavities 34, 56" and insert -- Cavities 32, 56 --, therefor.

In Column 7, Line 5, delete "threaded portion 74" and insert -- threaded portion 75 --, therefor.

In Column 7, Line 7, delete "outer surface 76" and insert -- outer surface 77 --, therefor.

In Column 7, Line 9, delete "surface 76" and insert -- surface 77 --, therefor.

In Column 7, Lines 9-10, delete "flange 78" and insert -- flange 79 --, therefor.

In Column 7, Line 10, delete "flange 78" and insert -- flange 79 --, therefor.

Signed and Sealed this
Twentieth Day of March, 2018

Andrei Iancu
*Director of the United States Patent and Trademark Office*

CERTIFICATE OF CORRECTION (continued)
U.S. Pat. No. 9,730,806 B2

In Column 7, Line 12, delete "flange 78" and insert -- flange 79 --, therefor.

In Column 7, Line 47, delete "surfaces 100, 102, 104" and insert -- surfaces 102, 104, 106 --, therefor.

In Column 9, Line 44, delete "threaded portion 74" and insert -- threaded portion 75 --, therefor.

In Column 9, Line 62, delete "flange 78" and insert -- flange 79 --, therefor.